US009145539B2

(12) United States Patent
Turner et al.

(10) Patent No.: US 9,145,539 B2
(45) Date of Patent: Sep. 29, 2015

(54) SYSTEMS AND METHODS FOR POSITIONING FLEXIBLE FLOATING PHOTOBIOREACTORS

(75) Inventors: Christopher Wayne Turner, Windsor, CO (US); Bryan Rhea McCarty, Fort Collins, CO (US); Peter Allen Letvin, Fort Collins, CO (US); Bryan Dennis Willson, Fort Collins, CO (US); Daniel Robert Herboldsheimer, Fort Collins, CO (US)

(73) Assignees: SOLIX ALGREDIENTS, INC., Fort Collins, CO (US); COLORADO STATE UNIVERSITY RESEARCH FOUNDATION, Fort Collins, CO (US)

( * ) Notice: Subject to any disclaimer, the term of this patent is extended or adjusted under 35 U.S.C. 154(b) by 760 days.

(21) Appl. No.: 13/046,559

(22) Filed: Mar. 11, 2011

(65) Prior Publication Data

US 2011/0281340 A1   Nov. 17, 2011

Related U.S. Application Data

(60) Provisional application No. 61/313,474, filed on Mar. 12, 2010.

(51) Int. Cl.
*C12M 1/04* (2006.01)
*C12M 1/00* (2006.01)
*C12M 1/09* (2006.01)

(52) U.S. Cl.
CPC ............. *C12M 21/02* (2013.01); *C12M 23/26* (2013.01); *C12M 23/56* (2013.01); *C12M 39/00* (2013.01); *Y02E 50/17* (2013.01)

(58) Field of Classification Search
CPC ...... C12M 21/02; C12M 23/14; C12M 23/22; C12M 23/26; C12M 23/34; C12M 23/56
USPC ........................................ 435/292.1; 47/1.4
See application file for complete search history.

(56) References Cited

U.S. PATENT DOCUMENTS

| 2,732,663 | A |   | 1/1956 | Dewey |
| 3,955,317 | A | * | 5/1976 | Gudin ........................... 435/420 |

(Continued)

FOREIGN PATENT DOCUMENTS

| GB | 2235210 A | 2/1991 |
| JP | S50105881 A | 8/1975 |

(Continued)

OTHER PUBLICATIONS

International Search Report and Written Opinion issued in PCT/US2011/28207, mailed May 24, 2011, 11 pages.

(Continued)

*Primary Examiner* — William H Beisner
(74) *Attorney, Agent, or Firm* — Faegre Baker Daniels LLP

(57) ABSTRACT

A top reference photobioreactor system according to an embodiment of the present invention includes a flexible floating photobioreactor having a buoyancy tube filled with a gas that is less dense, and a ballast tube filled with a substance, such as saltwater, that is more dense, than the liquid in which the photobioreactor floats. A top reference photobioreactor method according to an embodiment of the present invention includes controlling a depth of the top reference photobioreactor by controlling a volume and/or density of ballast in the ballast tube and/or by controlling a volume and/or density of gas in the buoyancy tube.

26 Claims, 13 Drawing Sheets

(56) References Cited

U.S. PATENT DOCUMENTS

| | | | |
|---|---|---|---|
| 3,955,318 A | 5/1976 | Hulls | |
| 3,981,803 A | 9/1976 | Coulthard | |
| 4,149,589 A | 4/1979 | Hopman | |
| 4,201,525 A | 5/1980 | Brown et al. | |
| 4,241,724 A | 12/1980 | Hull | |
| 4,253,271 A | 3/1981 | Raymond | |
| 4,290,242 A | 9/1981 | Gregory, Jr. | |
| 4,320,594 A | 3/1982 | Raymond | |
| 4,324,068 A | 4/1982 | Anthony | |
| 4,368,056 A | 1/1983 | Pierce et al. | |
| 4,390,624 A | 6/1983 | Leavitt | |
| 4,473,970 A | 10/1984 | Hills | |
| 4,744,349 A | 5/1988 | Sorensen | |
| 4,879,232 A | 11/1989 | MacDonald et al. | |
| 4,910,912 A | 3/1990 | Lowrey, III | |
| 4,921,803 A | 5/1990 | Nohr | |
| 4,950,601 A | 8/1990 | MacDonald et al. | |
| 4,952,511 A | 8/1990 | Radmer | |
| 4,954,055 A | 9/1990 | Raible et al. | |
| 4,958,460 A | 9/1990 | Nielson et al. | |
| 4,997,347 A | 3/1991 | Roos | |
| 5,137,828 A | 8/1992 | Robinson et al. | |
| 5,250,427 A | 10/1993 | Weaver et al. | |
| 5,270,175 A | 12/1993 | Moll | |
| 5,534,417 A | 7/1996 | Arad et al. | |
| 5,536,398 A | 7/1996 | Reinke | |
| 5,573,669 A | 11/1996 | Jensen | |
| 5,591,341 A | 1/1997 | Jensen | |
| 5,597,731 A | 1/1997 | Young et al. | |
| 5,659,977 A | 8/1997 | Jensen et al. | |
| 5,661,017 A | 8/1997 | Dunahay et al. | |
| 5,778,823 A | 7/1998 | Adey et al. | |
| 5,846,816 A | 12/1998 | Forth | |
| 5,851,398 A | 12/1998 | Adey | |
| 5,910,254 A | 6/1999 | Guelcher et al. | |
| 5,958,761 A | 9/1999 | Yogev et al. | |
| 5,981,271 A | 11/1999 | Doucha et al. | |
| 6,000,551 A | 12/1999 | Kanel et al. | |
| 6,037,416 A | 3/2000 | Iwamoto et al. | |
| 6,083,740 A | 7/2000 | Kodo et al. | |
| 6,156,561 A | 12/2000 | Kodo et al. | |
| 6,174,720 B1 | 1/2001 | Oxley et al. | |
| 6,192,833 B1 | 2/2001 | Brune et al. | |
| 6,329,196 B1 | 12/2001 | Johnson et al. | |
| 6,348,347 B1 | 2/2002 | Hirabayashi et al. | |
| 6,370,815 B1 | 4/2002 | Skill et al. | |
| 6,395,521 B1 | 5/2002 | Miura | |
| 6,416,993 B1 | 7/2002 | Wexler et al. | |
| 6,485,229 B1 | 11/2002 | Gunderson et al. | |
| 6,492,149 B1 | 12/2002 | Muller-Feuga | |
| 6,524,486 B2 | 2/2003 | Borodyanski et al. | |
| 6,579,714 B1 | 6/2003 | Hirabayashi et al. | |
| 6,602,703 B2 | 8/2003 | Dutil | |
| 6,827,036 B2 | 12/2004 | Connolly | |
| 6,858,430 B1 | 2/2005 | Reddy et al. | |
| 6,986,323 B2 | 1/2006 | Ayers | |
| 7,056,725 B1 | 6/2006 | Lu | |
| 2002/0034817 A1 | 3/2002 | Henry et al. | |
| 2002/0064470 A1 | 5/2002 | Andersen et al. | |
| 2002/0072109 A1 | 6/2002 | Bayless et al. | |
| 2002/0079270 A1 | 6/2002 | Borodyanski et al. | |
| 2002/0108582 A1 | 8/2002 | Connolly | |
| 2003/0059932 A1 | 3/2003 | Craigie et al. | |
| 2003/0073231 A1 | 4/2003 | Dutil | |
| 2003/0180898 A1 | 9/2003 | Bailey et al. | |
| 2003/0228684 A1 | 12/2003 | Burbidge et al. | |
| 2004/0121447 A1 | 6/2004 | Fournier | |
| 2004/0129045 A1 | 7/2004 | Lee | |
| 2004/0254559 A1 | 12/2004 | Tanaami et al. | |
| 2005/0037480 A1 | 2/2005 | Chiueh | |
| 2005/0063250 A1 | 3/2005 | Hubbard | |
| 2005/0064577 A1 | 3/2005 | Berzin | |
| 2005/0095700 A1 | 5/2005 | Budzowski et al. | |
| 2005/0115893 A1 | 6/2005 | Brune et al. | |
| 2005/0239182 A1 | 10/2005 | Berzin | |
| 2005/0260553 A1 | 11/2005 | Berzin | |
| 2005/0266541 A1 | 12/2005 | Dillon | |
| 2005/0269259 A1 | 12/2005 | Dunlop et al. | |
| 2005/0279095 A1 | 12/2005 | Goldman | |
| 2006/0035370 A1 | 2/2006 | Lee et al. | |
| 2007/0048848 A1* | 3/2007 | Sears | 435/134 |
| 2009/0095692 A1 | 4/2009 | Tharp | |
| 2009/0130706 A1 | 5/2009 | Berzin et al. | |
| 2009/0232764 A1 | 9/2009 | Ober et al. | |
| 2009/0305389 A1 | 12/2009 | Willson et al. | |

FOREIGN PATENT DOCUMENTS

| | | | |
|---|---|---|---|
| JP | H01108973 A | 4/1989 | |
| JP | H04299975 A | 10/1992 | |
| JP | H10511854 A | 11/1998 | |
| JP | 2002507908 A | 3/2002 | |
| JP | 2007046056 A | 2/2007 | |
| JP | 2008107310 A | 5/2008 | |
| WO | 02099031 A1 | 12/2002 | |
| WO | 2005085413 A1 | 9/2005 | |
| WO | WO 2005121309 A1 * | 12/2005 | |
| WO | 2006020177 A1 | 2/2006 | |
| WO | WO 2008134010 A2 * | 11/2008 | |
| WO | 2009040383 A1 | 4/2009 | |
| WO | 2009090549 A2 | 7/2009 | |
| WO | WO 2009094196 A2 * | 7/2009 | |
| WO | 2009106836 A2 | 9/2009 | |

OTHER PUBLICATIONS

Belarbi, El Hassan et al., "A process for high yield and scaleable recovery of high purity eicosapentaenoic acid esters from microalgae and fish oil," Enzyme and Microbial Technology 26 (2000) 516-529.

International Preliminary Report on Patentability and Written Opinion issued for PCT/US2006/033252, mailed Mar. 6, 2008.

Sears, James T et al., "Mass Cultivation of Photosynthetic Algae for Biodiesel Feedstock via Linear-Peristaltic Thermal-Regulated Aseptic Photo-Bioreactors," presented Jul. 2006 at Solar 2006 Conference, Denver, Colorado.

Sears, Jim, Biodiesel from Algae: SunSource Business and Technology Review, SunSource Industries, CSU Engines & Energy Conversion Laboratory, Feb. 16, 2006, presented Jul. 2006 at Solar 2006 Conference, Denver, Colorado.

Sears, Jim, "Commercial Production of Biodiesel Fuel from Algae," presented Jul. 2006 at Solar 2006 Conference, Denver, Colorado, SunSource Industries, Jan. 5, 2006, version 2.2.

Sheehan, J. et al., "A Look Back at the U.S. Department of Energy's Aquatic Species Program—Biodiesel from Algae," National Renewable Energy Laboratory, U.S. Department of Energy's Office of Fuels Development, Jul. 1998, NREL/TP-580-24190 Close Out Report.

Solix Biofuels, UNFAO, "Biofuel Production Climate Change Mitigation Global Energy Independence," Aug. 12, 2006, presented Jul. 2006 at Solar 2006 Conference, Denver, Colorado.

* cited by examiner

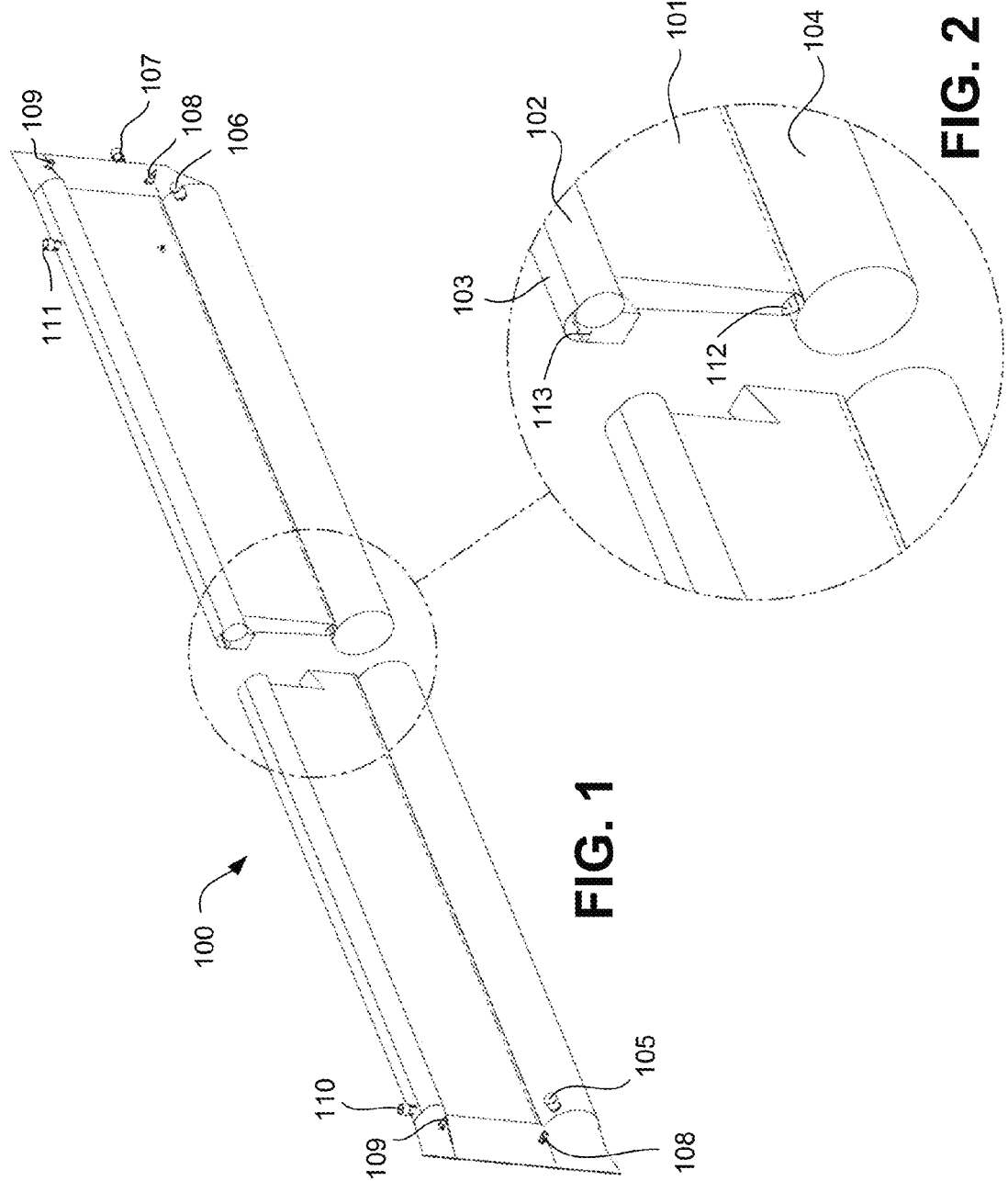

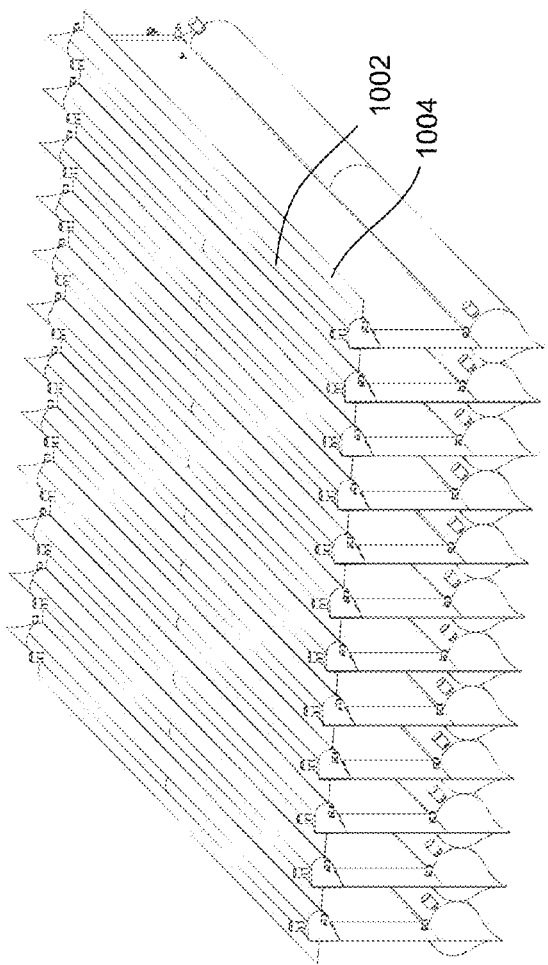

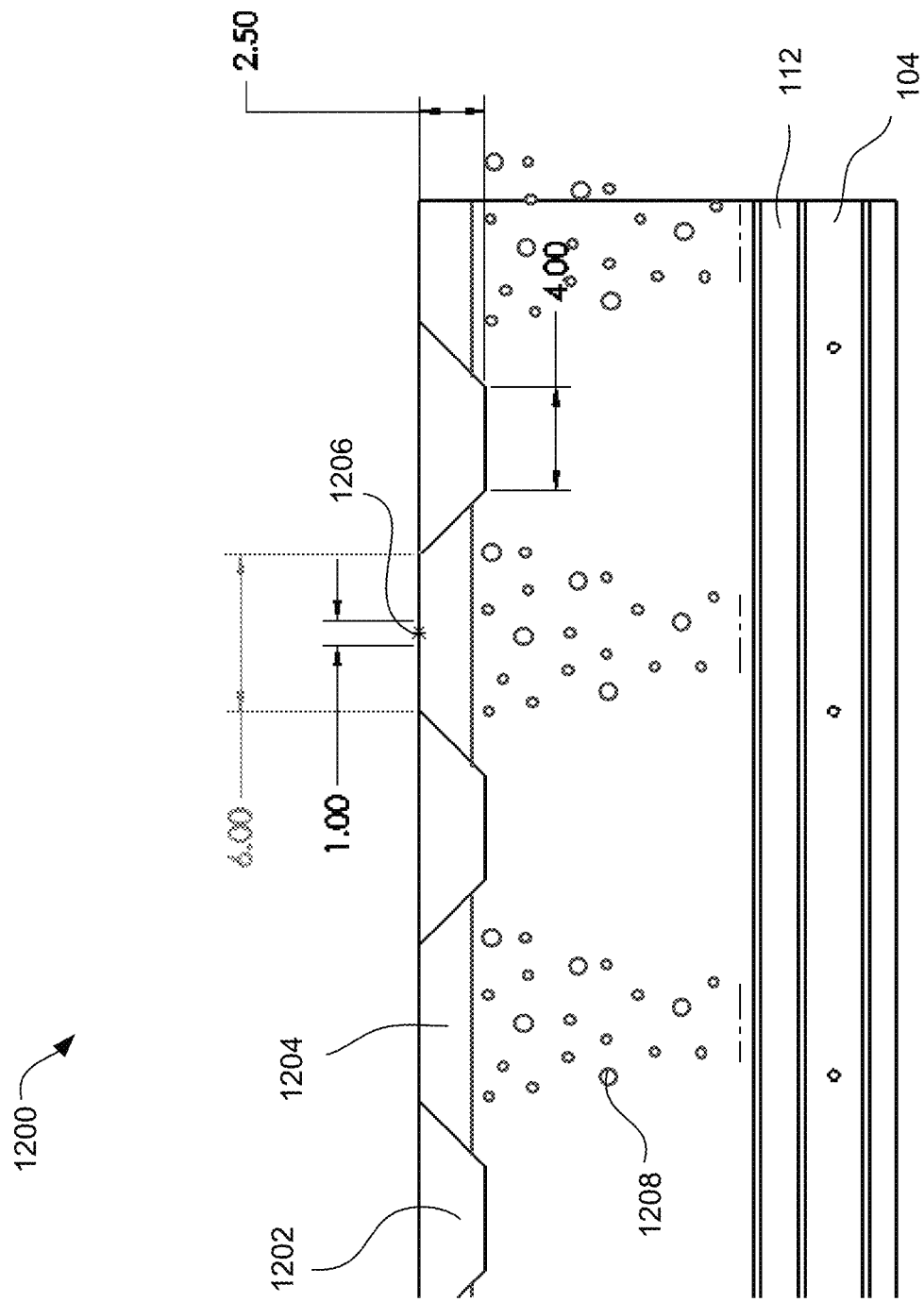

SYSTEMS AND METHODS FOR POSITIONING FLEXIBLE FLOATING PHOTOBIOREACTORS

CROSS-REFERENCE TO RELATED APPLICATION

This application claims the benefit of U.S. Provisional Patent Application Ser. No. 61/313,474, filed on Mar. 12, 2010, which is incorporated by reference herein in its entirety for all purposes.

TECHNICAL FIELD

Embodiments of the present invention relate generally to bioreactors, and more specifically to floating closed bioreactor panels.

BACKGROUND

Producing biofuels, such as biodiesel, bioethanol, and/or biogasoline, from renewable energy sources provides numerous benefits. The increasing costs, increasing difficulty of extraction, and depletion of known fossil fuel reserves help to spur the development of such alternative fuel supplies. Efforts have been made to develop renewable energy fuels such as ethanol from corn grain or biodiesel from canola, palm, rapeseed and other sources. The amount of biofuel that can be derived from food plant materials is often limited and the underlying increase in food commodity prices often negatively impacts food availability in developing countries, food prices in the developed world, on otherwise limited food-producing land.

Efforts are underway to generate biofuels and biochemicals from non-food materials, such as cellulosic ethanol from wood pulp, corn stover or sugar cane bagasse. Algae and other photosynthetic microorganisms can provide feedstock for biofuel and biochemical synthesis. Biofuel, biochemical, and biomass production from algae could permit productivities per unit of land area orders of magnitude higher than those of corn, rapeseed, palm, canola, sugar cane, and other traditional crops. In addition to biofuels, biochemicals and biomass can provide a variety of sustainable feedstock for plastics, chemical additives, essential human food supplements, and animal feedstock.

SUMMARY

Embodiments of the present invention include flexible and/or floating and/or film photobioreactor panels having a buoyancy tube to permit flotation of the photobioreactor panels. Such photobioreactors may include a buoyancy tube filled or partially filled with a gas, as well as a ballast tube filled with a material that is more dense than the surrounding fluid, to permit the flexible photobioreactor panel to be floated in a body of water while maintaining the photobioreactor panel in an upright or substantially upright configuration, in which the buoyancy tube is at the top or at the surface or closer to the surface, and in which the ballast tube is at the bottom, or further away from the surface.

Any known species of algae or photosynthetic or non-photosythetic microorganisms may be grown in a photobioreactor and utilize such containment strategies according to embodiments of the present invention. According to some embodiments of the present invention species such as but not limited to *Nannochloropsis oculata, Nannochloropsis gaditana, Nannochloropsis salina, Tetraselmis suecica, Tetraselmis chuii, Nannochloropsis* sp., *Chlorella salina, Chlorella protothecoides, Chlorella ellipsoidea, Dunaliella tertiolecta, Dunaliella salina, Phaeodactulum tricornutum, Botrycoccus braunii, Chlorella emersonii, Chlorella minutissima, Chlorella pyrenoidosa, Chlorella sorokiniana, Chlorella vulgaris, Chroomonas salina, Cyclotella cryptica, Cyclotella* sp., *Euglena gracilis, Gymnodinium nelsoni, Haematococcus pluvialis, Isochrysis galbana, Monoraphidium minutum, Monoraphidium* sp., *Neochloris oleoabundans, Nitzschia laevis, Onoraphidium* sp., *Pavlova lutheri, Phaeodactylum tricornutum, Porphyridium cruenturn, Scenedesmus obliquuus, Scenedesmus quadricaula Scenedesmus* sp., *Stichococcus bacillaris, Spirulina platensis, Thalassiosira* sp. may be grown, either separately or as a combination of species.

A photobioreactor system according to embodiments of the present invention includes a reservoir containing liquid, the liquid having a top surface level, a photobioreactor, wherein the photobioreactor is flexible and is floating in the liquid, the photobioreactor including a growth chamber containing media in which organisms may be grown, and a ballast chamber containing a fluid, the fluid having an effective density greater than that of the liquid, such that the ballast chamber exerts a force on the photobioreactor in a downward direction.

The photobioreactor system of any of paragraphs [0005] to [0007], wherein the fluid is a first fluid, wherein the effective density is a first effective density, wherein the force is a first force, and wherein the photobioreactor further includes a buoyancy chamber containing a second fluid, the second fluid having a second effective density less than that of the liquid, such that the buoyancy chamber exerts a second force on the photobioreactor in an upward direction.

The photobioreactor system of any of paragraphs [0005] to [0008], wherein the photobioreactor further includes a sparging chamber having a plurality of holes opening into the growth chamber, the sparging chamber containing a sparging gas or gas mixture that is configured to pass through the plurality of holes and rise through the media.

The photobioreactor system of any of paragraphs [0005] to [0009], wherein the top surface level is a reservoir top surface level, wherein the growth chamber comprises a head space above a media top surface level, and wherein the head space accommodates accumulation of the sparging gas or gas mixture.

The photobioreactor system of any of paragraphs [0005] to [0010], wherein the buoyancy chamber is isolated from, and directly adjacent to, the head space.

The photobioreactor system of any of paragraphs [0005] to [0011], wherein the ballast chamber is isolated from, and directly adjacent to, a bottom of the growth chamber.

The photobioreactor system of any of paragraphs [0005] to [0012], wherein the sparging chamber is located at a bottom of the growth chamber, and wherein the ballast chamber is isolated from, and directly adjacent to, the sparging chamber.

The photobioreactor system of any of paragraphs [0005] to [0013], wherein the ballast chamber and the buoyancy chamber maintain the photobioreactor in a substantially upright position as the photobioreactor is floating in the liquid.

The photobioreactor system of any of paragraphs [0005] to [0014], wherein the reservoir is a body of water selected from the group consisting of: an ocean, a lake, a sea, a pond, a river, a basin, a tub, a pool, and a tank.

The photobioreactor system of any of paragraphs [0005] to [0015], wherein the reservoir is a naturally occurring body of water.

The photobioreactor system of any of paragraphs [0005] to [0016], wherein the first fluid is salt water, and wherein the second fluid is air.

The photobioreactor system of any of paragraphs [0005] to [0017], wherein the ballast chamber comprises at least one port through which the fluid may be added to or removed from the ballast chamber.

The photobioreactor system of any of paragraphs [0005] to [0018], wherein the buoyancy chamber comprises at least one port through which the second fluid may be added to or removed from the buoyancy chamber.

The photobioreactor system of any of paragraphs [0005] to [0019], wherein the photobioreactor is one of a plurality of photobioreactors each substantially the same as the photobioreactor, wherein the plurality of photobioreactors is floating in the liquid, and wherein the plurality of photobioreactors are positioned one next to the other such that a spacing between two adjacent photobioreactors of the plurality of photobioreactors is determined by widths of adjacent abutting ballast chambers.

The photobioreactor system of any of paragraphs [0005] to [0020], wherein each of the plurality of photobioreactors comprises a top flap, wherein the top flap is configured to be placed over a top of an adjacent photobioreactor or over the top surface level of the liquid between adjacent photobioreactors.

The photobioreactor system of any of paragraphs [0005] to [0021], wherein the photobioreactor is at least partially formed of a substantially transparent plastic film.

The photobioreactor system of any of paragraphs [0005] to [0022], wherein the photobioreactor is at least partially formed of or coated by one or more anti-biofouling additives selected from the group consisting of: polyethylene glycol (PEG), hyperbranched fluoropolymer (HBFP), polyethylene (PE), polyvinyl chloride (PVC), polymethylmethacrylate (PMMA), natural rubber (NR), polydimethylsiloxane (PDMS), polystyrene (PS), perfluoropolyether (PFPE), polytetrafluoroethylene (PTFE), and silicons and derivatives.

The photobioreactor system of any of paragraphs [0005] to [0023], wherein the media comprises one or more anti-biofouling additives selected from the group consisting of: polyethylene glycol (PEG), silicons and derivatives, biocides, fluorocarbons, and quatinary amines.

The photobioreactor system of any of paragraphs [0005] to [0024], wherein at least a bottom surface of the ballast chamber is reinforced to minimize possible puncture.

A method for algae growth containment according to embodiments of the present invention includes floating a photobioreactor in a reservoir containing liquid, the liquid having a top surface level, wherein the photobioreactor is flexible and comprises a growth chamber and a ballast chamber, adding media to the growth chamber, wherein the media is adapted to support a suspension culture of algae, and adding fluid to the ballast chamber, wherein the fluid has an effective density greater than that of the liquid, such that the ballast chamber exerts a force on the photobioreactor in a downward direction.

The method of paragraph [0026], wherein the fluid is a first fluid, wherein the effective density is a first effective density, wherein the force is a first force, and wherein the photobioreactor further includes a buoyancy chamber, the method further including adding a second fluid to the buoyancy chamber, wherein the second fluid has a second effective density less than that of the liquid, such that the buoyancy chamber exerts a second force on the photobioreactor in an upward direction.

The method of paragraphs [0026] or [0027], wherein the reservoir is an ocean, the method further including growing the suspension culture of algae in the media, and mixing the suspension culture of algae by floating the photobioreactor in a manner that permits the photobioreactor to move in response to waves in the ocean.

The method of any of paragraphs [0026] to [0028], wherein the photobioreactor is one of a plurality of substantially similar photobioreactors, the method further including placing the plurality of substantially similar photobioreactors in a side-by-side configuration floating in the liquid, and adjusting a spacing between adjacent photobioreactors by adding the fluid to, or subtracting the fluid from, the ballast chambers of adjacent photobioreactors.

The method of any of paragraphs [0026] to [0029], further including adjusting a depth of the photobioreactor in the liquid by adding the fluid to, or subtracting the fluid from, the ballast chamber.

The method of any of paragraphs [0026] to [0030], further including adjusting a depth of the photobioreactor in the liquid by adding the second fluid to, or subtracting the second fluid from, the buoyancy chamber.

The method of any of paragraphs [0026] to [0031], further including subtracting the second fluid from the buoyancy chamber until the photobioreactor is substantially submerged below the top surface level.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 1 illustrates a foreshortened front side perspective view of a photobioreactor, according to embodiments of the present invention.

FIG. 2 illustrates an enlarged partial cross-sectional view of the photobioreactor of FIG. 1, according to embodiments of the present invention.

FIG. 10 illustrates an end view of a photobioreactor with top flaps, according to embodiments of the present invention.

FIG. 11 illustrates a plurality of photobioreactors placed side-by-side with top flaps, according to embodiments of the present invention.

FIG. 12 illustrates an alternative photobioreactor, according to embodiments of the present invention.

Figure 4:
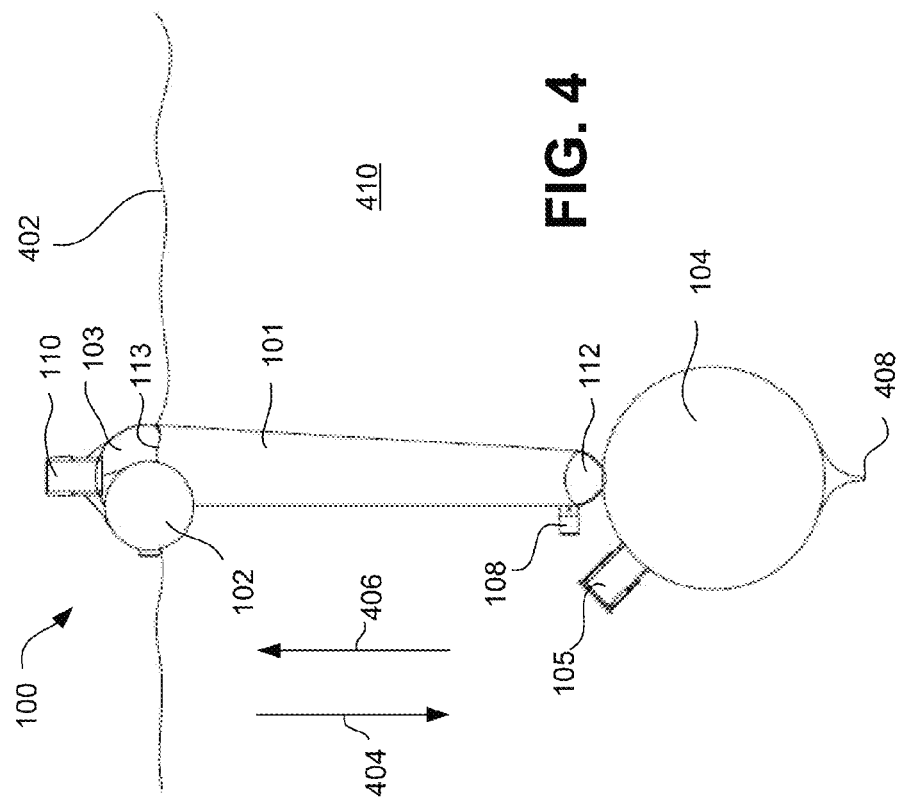
FIG. 4 illustrates a sectional end view of the photobioreactor of FIG. 1, according to embodiments of the present invention.
Figure 3:
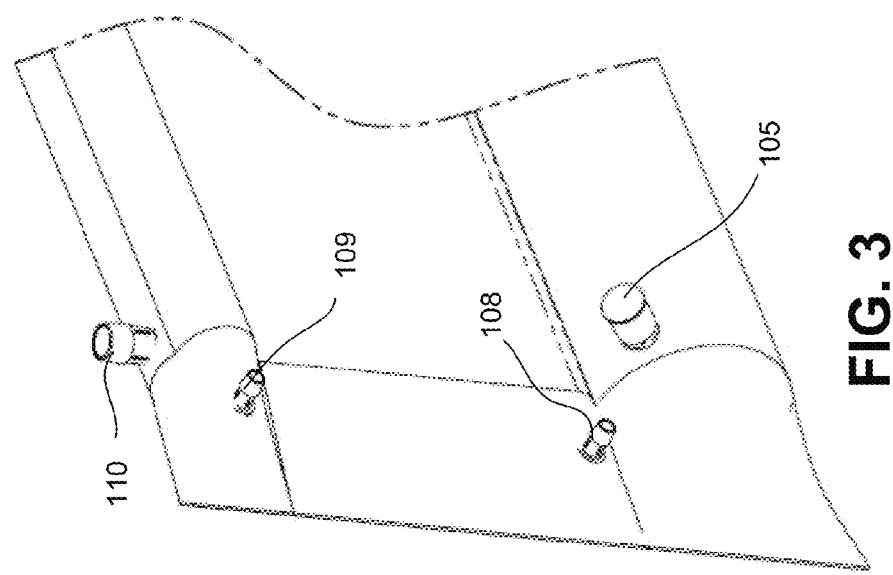
FIG. 3 illustrates an enlarged partial perspective view of an end of the photobioreactor of FIGS. 1 and 2, according to embodiments of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Researchers are exploring growing algae as a feedstock for biodiesel. In many designs the algae is grown inside closed bioreactors comprised of glass or plastic, either rigid or flexible. Examples of closed system bioreactors suitable for growth of algae and other microorganisms are described in U.S. Patent Application Publication No. 2008/0160591, published Jul. 3, 2008 (the "'591 Publication"), and International Publication No. WO 2010/108049 A1, published on Sep. 23, 2010 (the "'049 Publication") and International Publication No. WO 2010/151606 A1, published on Dec. 29, 2010 (the "'606 Publication"), all of which are incorporated by reference herein in their entireties.

The total life cycle cost of a closed bioreactor depends on various factors but is generally significantly more per mass unit of biomass produced than an open pond or reservoir, based on previous traditional construction approaches and materials. Despite traditionally offering very high productivity, clear rigid tubes mounted on a rack in a greenhouse are often even more costly on a life cycle basis.

As described in the '591 Publication, the '049 Publication, and the '606 Publication, a clear thin flexible closed clear plastic photobioreactor panel may be suspended in a water bearing basin or reservoir tethered to the basin bottom, for example with pipe ballast, to facilitate growth and harvest methodology improvements, resulting in significant cost reduction over traditional clear rigid tube designs. As used herein, the term "reservoir" is used in its broadest sense to refer to any body of water, whether large (e.g. ocean) or small (e.g. pond or tank), and whether naturally-occurring (e.g. lake) or artificial or man-made (basin).

Embodiments of the present invention may exhibit structure and algal containment systems similar to those described in the '591 Publication, the '049 Publication, and the '606 Publication. Embodiments of the present invention may incorporate a buoyancy tube at the top and ballast tube at the bottom of the closed photobioreactor panel, which provides a very cost effective means to stably suspend the panel in terrestrial-based basin water or permit deployment in a shallow or deep body of water, lake, lagoon, or other body of water. Additionally, embodiments of the present invention include diffuse light enhancements, biofouling countermeasures, evaporation countermeasures, and gas reuse provisions incorporated into the design in order to bundle system enhancements into a single generational step in the technology. Additionally, a top reference panel photobioreactor system does not require grading or leveling of earthen surfaces, according to embodiments of the present invention.

The following is a brief description of an embodiment of a top referenced photobioreactor 100, illustrated in FIGS. 1-4. As used herein, the term "top reference photobioreactor" is used in its broadest sense to refer to a photobioreactor that is capable of floating in water, and which has a buoyancy element and a ballast element. The buoyancy element will typically be at or near the top of the photobioreactor, and the ballast element will typically be at or near the bottom of the photobioreactor, although other configurations are possible to maintain the photobioreactor in an upright and/or semi-upright position as it floats, according to embodiments of the present invention. The bioreactor 100 may include a microorganism containment chamber 101, which may also be referred to as a growth chamber, a buoyancy tube 102, an exhaust chamber 103 which may also be referred to as a head space, a ballast chamber 104, a ballast chamber fill port 105, 106, a harvest/innoculation port 107, a sparge gas supply port 108, a buoyancy chamber supply port 109, exhaust/intake ports 110, 111 and/or a sparge chamber 112, according to embodiments of the present invention.

The photobioreactor 100 may be made from various layers of transparent, semi-transparent, reflective, semi-reflective, opaque colored, translucent colored, and/or surface treated (to create a pattern or texture) film, selectively welded together to form the various chambers, according to embodiments of the present invention. This minimizes the cost to produce photobioreactors, which are thus flexible. FIG. 4 shows a bottom seam 408 where the two bottom edges of two layers were welded together to form the bottom of the ballast chamber 104, according to embodiments of the present invention.

When the photobioreactor 100 is deployed, the photobioreactor (which may be made from a flexible membrane or film composed of LDPE, HDPE, Nylon, Mylar, PVC, or similar material) is placed into a reservoir (e.g. a basin of water). This basin can be man-made via earthen berm or the like, or it can be a lake, harbor or any other body of water. The buoyancy tube 102 is filled with gas (e.g. air, $CO_2$, stack gas, or the like) to a given pressure through the buoyancy fill port 109, according to embodiments of the present invention. In one embodiment this tube 102 is approximately 2.5" inches diameter and is filled with gas to a pressure of between 1 and 4 psi. This tube 102 may be larger or smaller in diameter depending on the size and weight of the material in the ballast tube, according to embodiments of the present invention. When the volume of gas in this tube 102 is buoyant enough, the buoyancy will lift the ballast tube 104 off the bottom of the water basin. Once the buoyancy tube 102 is filled, the ports 109 connected to this tube can be plugged in order to deter any of the gas in this tube 102 from leaking out. Alternatively, the port 109 can be connected to a pressure source (accumulator, pressurized vessel, pump, blower, and the like) in order to maintain pressure in this tube 102. If the air supply to the buoyancy tube is connected via a check valve, the buoyancy tube 102 will stay inflated even if the pressure source fails, according to embodiments of the present invention.

The ballast tube 104 may then be filled via the ballast inlet port 105, according to embodiments of the present invention. The material or liquid that is pumped into the ballast tube 104 has a density greater than the water comprising the body of water in which the photobioreactor system 100 floats. This liquid can be a brine, sugar solution, sand slurry, and/or any other higher density liquid or gel, according to embodiments of the present invention. In some embodiments, this ballast can be composed of a solid material (e.g. pipe, rocks, sand, concrete, and the like). In one embodiment, 2.5 lbs of salt is added to every gallon of fresh water to make a brine solution that is pumped into the ballast tube 104. In another embodiment, 2.0 lbs of salt is added to every gallon of fresh water to make a brine solution that is pumped into the ballast tube 104.

The density of the ballast tube is approximately 1.17 kg/L while the basin water is made of fresh water or sea water having a density between approximately 1 kg/L-1.03 kg/L, according to embodiments of the present invention. As the ballast tube 104 is filled, the end being filled with the ballast solution begins to sink until the film making up the algae containment chamber 101 is made taught, at least on one side, between the ballast tube 104 and the buoyancy tube 102, according to embodiments of the present invention. Any gas (e.g. air) that is in the ballast tube 104 as it is being filled is forced to the other end of the ballast tube 104, longitudinally speaking, and can be ejected from the system 100 via a ballast port 106, according to embodiments of the present invention. Once the ballast tube 104 is filled, the one or more ballast ports 105, 106 may be plugged in order to deter any of the ballast liquid from leaking into the surrounding basin. In one embodiment, for example the embodiment shown in FIG. 9, the ballast tubes 904a, 904b each have a diameter of approximately six inches so that when multiple panels 900a, 900b are placed side by side, the spacing of the panels will be approximately six inches, and/or no less than six inches, according to embodiments of the present invention. The spacing D between adjacent photobioreactors 900a, 900b will be approximately the same as the diameter of the ballast chambers 904a, 904b, according to embodiments of the present invention. If the panels are packed tightly enough in the water basin, the spacing between adjacent panels is equal to the diameter of the ballast tube, for example six inches, according to embodiments of the present invention.

Figure 20:
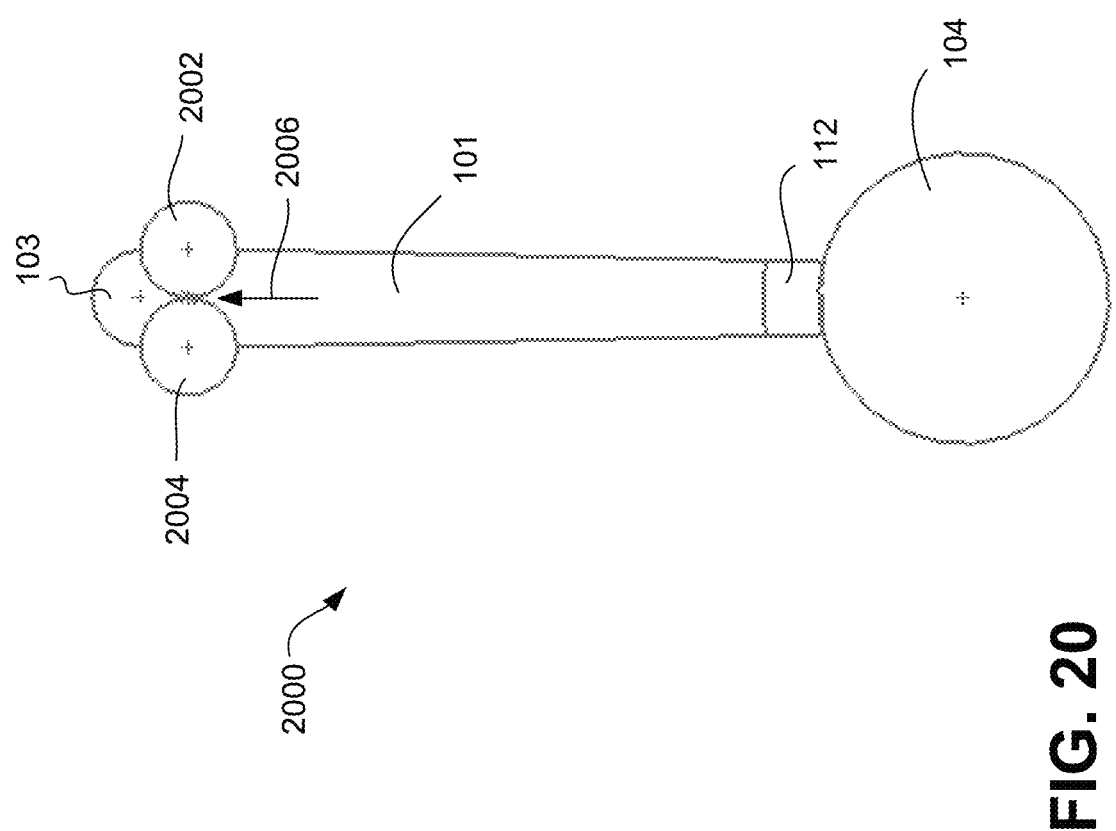
FIG. 20 illustrates a sectional view of a photobioreactor with dual buoyancy chambers, according to embodiments of the present invention.

According to one alternative embodiment of the present invention illustrated in FIG. 20, a photobioreactor 2000 may include two buoyancy tubes 2002, 2004. The head space 103 is located above the growth chamber 101, and the sparge gas is able to pass between the buoyancy tubes 2002, 2004 into the head space 103 as indicated by arrow 2006, according to embodiments of the present invention.

Figures 5, 6:
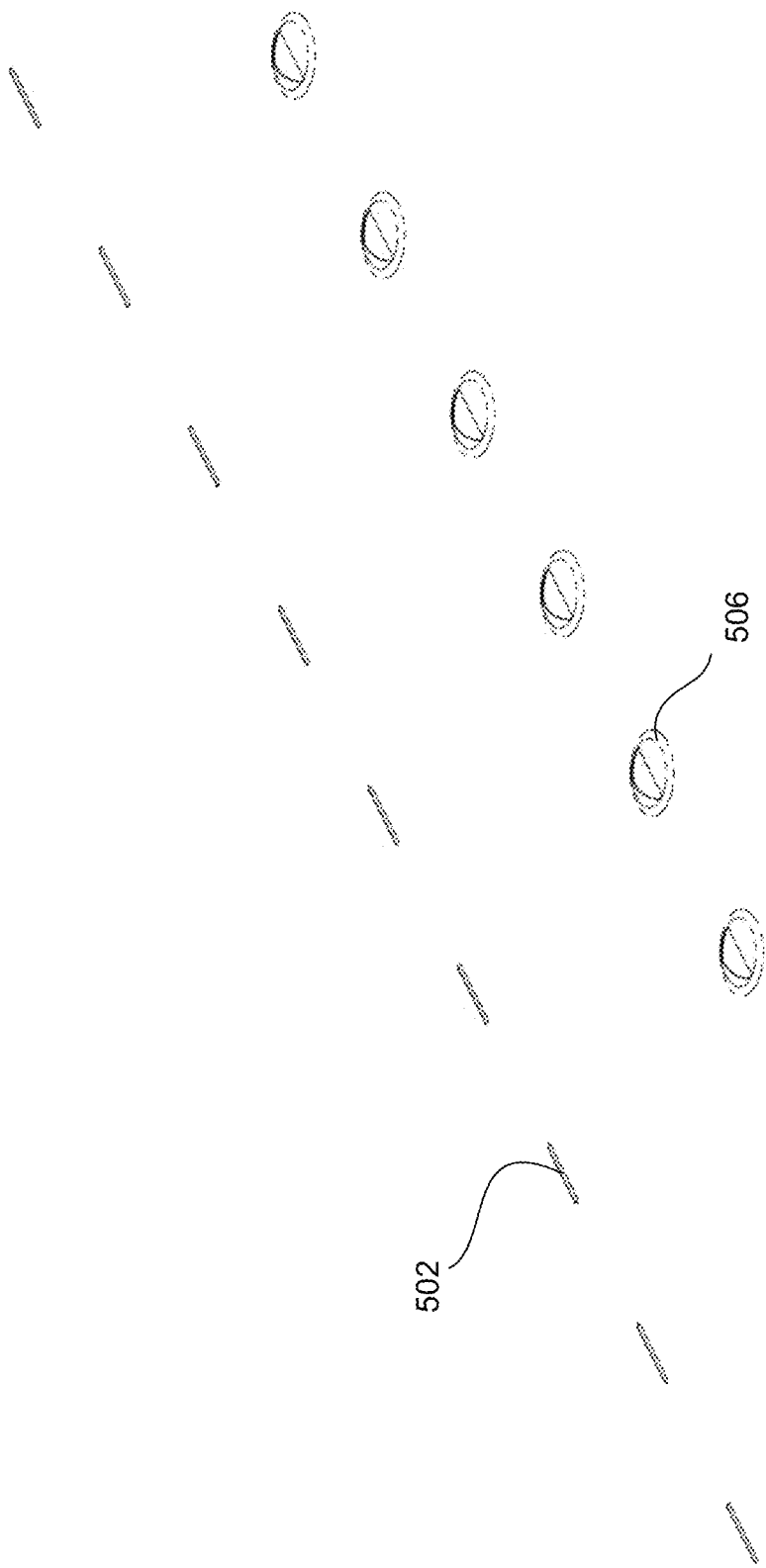
FIG. 5 illustrates a row of slits that may be formed on a sparging chamber, according to embodiments of the present invention.
FIG. 6 illustrates the row of slits of FIG. 5 in a flowing condition, according to embodiments of the present invention.
Figure 8:
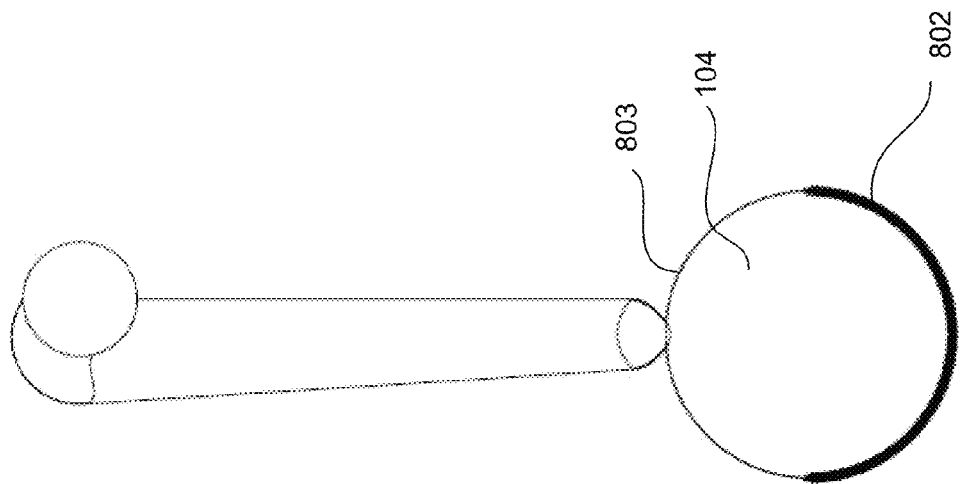
FIG. 8 illustrates a sectional end view of a photobioreactor with a reinforced ballast chamber bottom, according to embodiments of the present invention.
Figure 7:
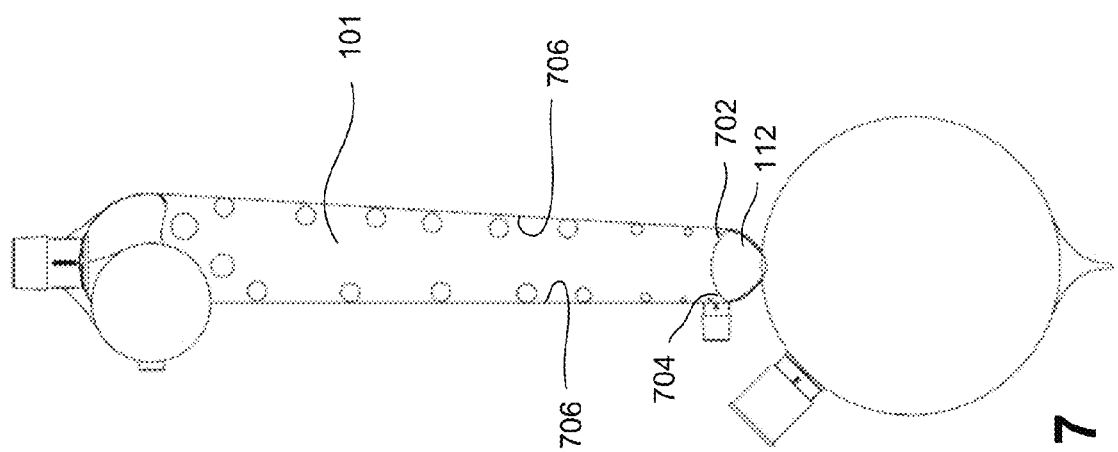
FIG. 7 illustrates a sectional end view of a photobioreactor, showing sparging chamber hole placement for mixing and/or anti-fouling benefits, according to embodiments of the present invention.

The microorganism containment chamber 101 may then be filled with media through harvest/inoculation port 107. In one embodiment this media is designed for the growth of microalgae but could also be designed for the growth of other microorganisms such as bacteria, cyanobacteria, and the like. The algae in this portion of the panel 101 is mixed and fed $CO_2$ by bubbling a $CO_2$ enriched gas through a sparge port 108 into the sparge tube 112, which may, for example, run along an entire length of the photobioreactor 100, according to embodiments of the present invention. The $CO_2$ can come from a coal fired power plant, a brewery, a cement factory, $CO_2$ from air extraction devices, or similar plant that produces an enriched $CO_2$ gas stream. The sparge tube 112 contains small perforations that allow the gas in the sparge tube 112 to flow into and through the algae/media mixture in the form of bubbles. As illustrated in FIGS. 5 and 6, these perforations can be small holes, for example slits 502 and/or semi-circular flaps. These bubbles travel from the sparge tube 112, located at the bottom of the algae chamber 101 to the top of the algae chamber 101. As these bubbles travel through the media, the water contacted by these bubbles is circulated. This circulation helps to reduce nutrient gradients in the media, circulate the algae from light to dark parts of the reactor, keep the algae suspended in the photobioreactor, remove $O_2$, reduce thermal stratification, and the like. As illustrated in FIG. 7, if the perforations are placed toward the inner walls 706 of the growth chamber 101, at locations such as location 702 and location 704, the sparge bubbles may also help to scrub and/or de-foul the inner surface of the side walls 706, in addition to potential circulation, mixing, and $O_2$ removal benefits.

Once the bubbles break at the free surface 113 of the media, the gas flows down the length of the exhaust tube 103 to one of the exhaust ports 110, 111, according to embodiments of the present invention. In one embodiment the exhaust tube 103 is located adjacent to the buoyancy tube 102 so that as long as the buoyancy tube 102 is inflated, the exhaust tube 103 will stay above the basin water level. The pressure of the exhaust tube 103 may be kept at atmospheric pressure, according to embodiments of the present invention. Because of the exhaust tube 103 location and pressure it does not add additional buoyant force to the photobioreactor 100, according to embodiments of the present invention. This may help to maintain a desired panel location and/or depth in the water. In other words, as the sparge gas flow rate is adjusted or even turned off, the buoyancy of the panel does not change, resulting in a stable panel depth in the water, according to embodiments of the present invention.

FIG. 4 illustrates a reservoir containing liquid 410, the liquid 410 having a top surface level 402, a photobioreactor 100, wherein the photobioreactor is flexible and is floating in the liquid 410, the photobioreactor including a growth chamber 101 containing media in which organisms may be grown, and a ballast chamber 104 containing a fluid, the fluid having an effective density greater than that of the liquid 410, such that the ballast chamber 104 exerts a force on the photobioreactor 100 in a downward direction, as indicated by arrow 404. FIG. 4 also illustrates a buoyancy chamber 102 containing another fluid, for example air, such that the buoyancy chamber 102 exerts a second force on the photobioreactor in an upward direction, as indicated by arrow 406. These buoyancy forces help to maintain the photobioreactor 100 in an upright position, as illustrated in FIG. 4, according to embodiments of the present invention.

Figure 18:
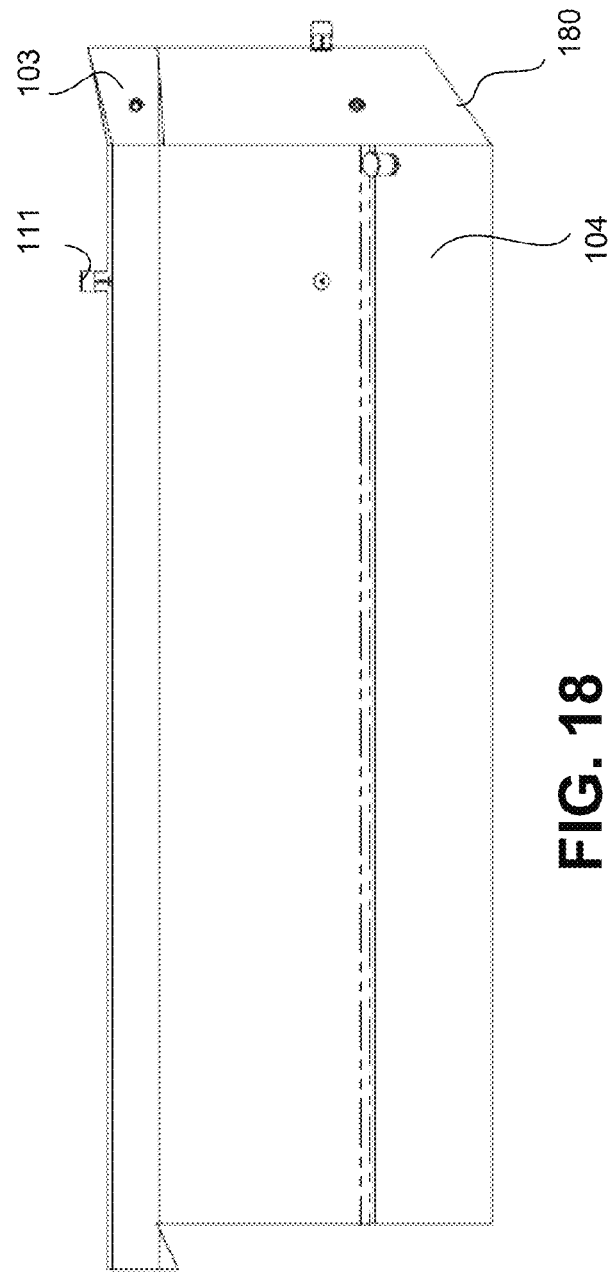
FIG. 18 illustrates a partial side elevation view of a tapered ballast tube end of a photobioreactor, according to embodiments of the present invention.

In one embodiment (not shown), the portion of the exhaust tube 103 and the buoyancy tube 102 located at one end of the photobioreactor 100 will exist without a ballast tube 104, or with a ballast tube of reduced diameter, directly underneath it. FIG. 18 illustrates a ballast chamber 104 having a tapered end at location 180, which is configured to provide less ballast in the region below exhaust port 111. In the event that the rest of the photobioreactor becomes submerged, the accumulated sparge gas will accumulate toward the end of the photobioreactor with the tapered ballast chamber 104, which will be higher in the water than the rest of the photobioreactor due to having less ballast at that location. In other words, this biases that portion of the panel 100 to sit higher in the basin than the rest of the photobioreactor. Hence, if a leak were to develop in the buoyancy tube 102 that caused the photobioreactor 100 to inadvertently sink, these unballasted (or reduced ballast) ends would trap air in the exhaust tube 103 behind exhaust port 111 (which is essentially the empty space, or "head space," in the chamber 101 above the media free surface 113) and the panel 100 would stay above the basin water surface, according to embodiments of the present invention. Keeping the exhaust ports 110, 111 above the basin water level minimizes or prevents the chance that basin water enters the photobioreactor, or that media escapes into the basin water, according to embodiments of the present invention.

In some instances, it may be desirable to allow the photobioreactors 100 to sink under the water in order to avoid damage due to inclement weather such as hail, wind storms, and the like. This can be accomplished by evacuating some or all of the gas out of the buoyancy tube 102, causing a net downward force caused by the ballast tube 104. The ballast tube 104 will then sink, for example to the bottom of the water basin. The various ports described herein may be attached to tubes for the addition and/or subtraction and/or flow of gases or fluids; as such, the fluids in the ballast tube 104 and the buoyancy tube may be controlled so as to keep the exhaust gas port 111 above the top surface level of the water (or other liquid) in the reservoir in which the photobioreactor floats, regardless of whether the rest of the photobioreactor is being submerged or floated, according to embodiments of the present invention.

Figure 19:
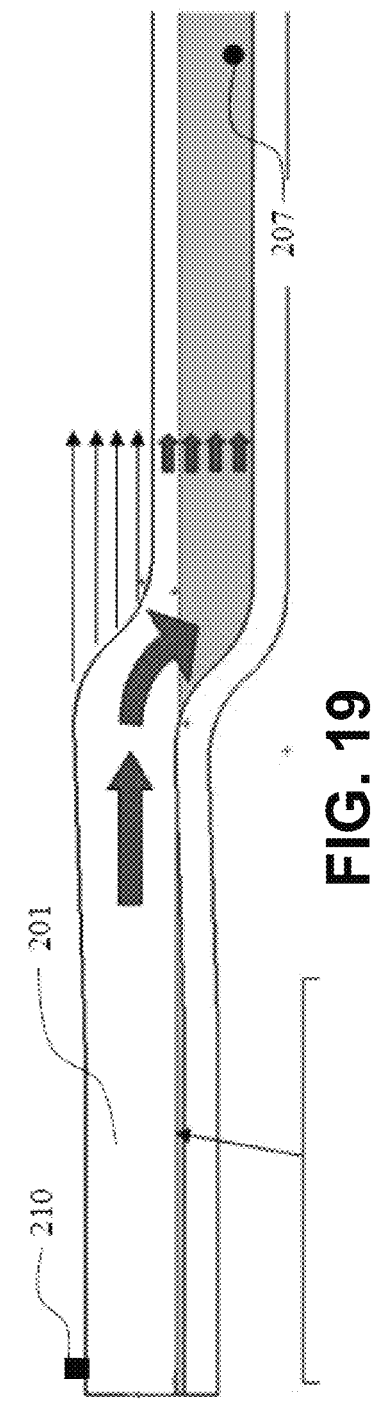
FIG. 19 illustrates a side elevation view of a photobioreactor depicting a harvesting procedure, according to embodiments of the present invention.

As illustrated in FIG. 19, another instance where it may be desirable to sink the photobioreactor to the bottom of the basin is during a harvest of the media within the chamber 201. Specifically, once the gas from the buoyancy tube 102 is evacuated causing the photobioreactor 100 to sink to the bottom of the basin, gas can be forced into one side of the algae containment chamber 201 through an exhaust port 210. This will cause this side of the photobioreactor (the side opposite to the harvest port) to lift forcing the algae and media in the algae containment chamber toward the other side of the reactor where it can be extracted through a harvest/inoculation port 207, according to embodiments of the present invention.

A photobioreactor system according to one embodiment of the present invention includes a clear flexible wall integrated containment vessel set that contains a buoyancy chamber (e.g. a tube filled with air on top), an algal broth containment chamber with an exhaust gas region adjacent to the buoyancy chamber above the algal broth, a sparge gas chamber (e.g. a tube under the algal broth containment) and a ballast containment chamber at the bottom containing a material (e.g. salt and water and/or sand and water and/or other higher mass density that flows for filling and makeup purposes) with a mass density in excess of fresh or sea water such that when each chamber is filled to the appropriate level, the vessel 100 floats in the water level to the water surface and at a height commensurate with the buoyancy force's equilibrium.

Such an embodiment provides for the operation in growth mode as a floating containment. In lifted harvest mode it provides for the filling of the algal harvest containment vessel with gas (e.g. air and/or $CO_2$ and/or $N_2$ and the like) starting at one end of the containment creating a lifting of the entire vessel to a sufficient height to cause flow of the algal broth to the opposite end of the containment for gravity or pumped removal for harvest. In the plug flow design, it provides the same service as the growth mode except that it can accept a periodic inflow and outflow of media and algal broth by expanding and contracting the algal broth containment to manage the flow and maintain a floating stable position, according to embodiments of the present invention. Such a design eliminates or reduces the cost associated with attaching an expensive ballast pipe to the bottom of the photobioreactor, including labor to assemble, attachment materials, and basin bottom flatness to ensure a level panel so that exhaust flow is not impeded. Impeding exhaust flow may cause undesirable lifting of vessels and algal spillage and loss. A top reference photobioreactor may also permit non-land based deployments and avoidance of earthwork costs.

The buoyancy chamber can be inflated and deflated (for example by adding or subtracting the air or other gas used to fill the buoyancy chamber) to control the depth of the overall vessel 100 as well as allow it to sink below the surface 402 of the water or to the bottom of the basin or lagoon, according to embodiments of the present invention. This provides for protection of the photobioreactor vessel 100 during inclement or stormy weather, wind, hail, snow, and the like. Submerging the photobioreactor 100 in this fashion also facilitates a periodic cleaning of the external area which is normally exposed to air, by allowing water to wash off accumulated debris, according to embodiments of the present invention.

The exhaust area 103 above the algal broth 101 is kept above the water basin (or similar body of water) by way of the buoyancy chamber 102, which allows the exhaust chamber 103 to maintain adequate flow area for the exhaust gases to escape from the photobioreactor 100 without creating significant back pressure due to flow losses, according to embodiments of the present invention. This placement provides for a non-obstructed containment exhaust route with minimal backpressure, according to embodiments of the present invention. Such a placement minimizes undesirable inflation and subsequent flotation of the growth chamber 101, which may cause a loss of algal broth to the connecting exhaust port 111, as well as poor sparge control and overall containment instability.

The exhaust discharge outlet 111 is positioned in such a way so as to stay above the external water surface 402, according to embodiments of the present invention. In the event of a system gas feed failure and subsequent restart of gas feed, this configuration prevents the exhaust discharge outlet 111 from having to be cleared of algal broth either manually or by a separate mechanism in order to restore exhaust function, according to embodiments of the present invention.

According to some embodiments of the present invention, the geometry of sparge holes (holes made between the sparge tube 112 and the growth chamber 101) are made in a shape that causes flexing or opening expansion during sparging to break bridging or build up around the sparge holes, to minimize biofouling flow restriction. As illustrated in FIGS. 5 and 6, such sparge holes may be slits 502 rather than round holes, and could also be formed in other shapes, according to embodiments of the present invention. Biofouling and salts precipitation has a tendency to build up around and over the sparge holes in some circumstances. A slit 502 has the characteristic of flexing when pressurized as illustrated by open slit 506 and closing when not pressurized as illustrated by closed slit 502, thus preventing back flow as well as reducing biofouling, according to embodiments of the present invention.

As shown in FIG. 7, sparge hole placement may be done strategically in order to maximize mixing and provide for bubble size and velocity to be close to the algal containment wall 706 to provide a hydrodynamic scrubbing of the wall 706, according to embodiments of the present invention. This may reduce or remove biofouling to the degree that it minimizes occluded light penetration into the algal broth, according to embodiments of the present invention. Embodiments of the present invention provide a mechanism of scrubbing with bubbles that is very cost effective compared with manual mechanical or chemical processes.

Additives to the material of the containment vessel can be used to suppress biofouling of the algal broth, sparge gas, ballast and bouyancy containment areas, according to embodiments of the present invention. Hydrophobic, hydrophylic, low adhesion, and/or toxic additives may be added to the material of the containment vessel, for example polyethylene glycol (PEG), hyperbranched fluoropolymer (HBFP), polyethylene (PE), polyvinyl chloride (PVC), polymethylmethacrylate (PMMA), natural rubber (NR), polydimethylsiloxane (PDMS), polystyrene (PS), perfluoropolyether (PFPE), polytetrafluoroethylene (PTFE), silicons and derivatives, and the like. Corona treatment of film may also be used to make the surface of film more hydrophilic, according to embodiments of the present invention.

Additives to the algal broth and/or media can be employed to suppress biofouling and foaming of the algal broth, according to embodiments of the present invention. Hydrophobic, hydrophylic, low adhesion, and/or toxic additives may be added to the algal broth and/or media, for example PEG, silicons and derivatives, biocides, fluorocarbons, quatinary amines, according to embodiments of the present invention.

Additives and surface treatments to the containment vessel surfaces can be employed to increase light levels and optimize light distribution to maximize growth, according to embodiments of the present invention. White surfaces, semi-reflective, tailored opaque and/or textured surfaces increase the diffuse light level for a given photosynthetically active radiation ("PAR") level. Algae is considerably more efficient at using less than full sunlight to maximize growth and minimize photo inhibition. The substitution of white plastic 803 in place of the clear plastic on the ballast chamber 104 provides a curved reflective surface to scatter and diffuse a greater amount of light than having a clear surface with an earthen color to the ballast, according to embodiments of the present invention. The bottom 802 of the ballast chamber 104 may also be reinforced, for example with an extra layer or a thicker layer, in order to better resist puncture. The white plastic 803 may also serve to replace a white liner in the bottom of the basin to reflect light, which may reduce the cost of the lining method, according to embodiments of the present invention.

Figure 9:
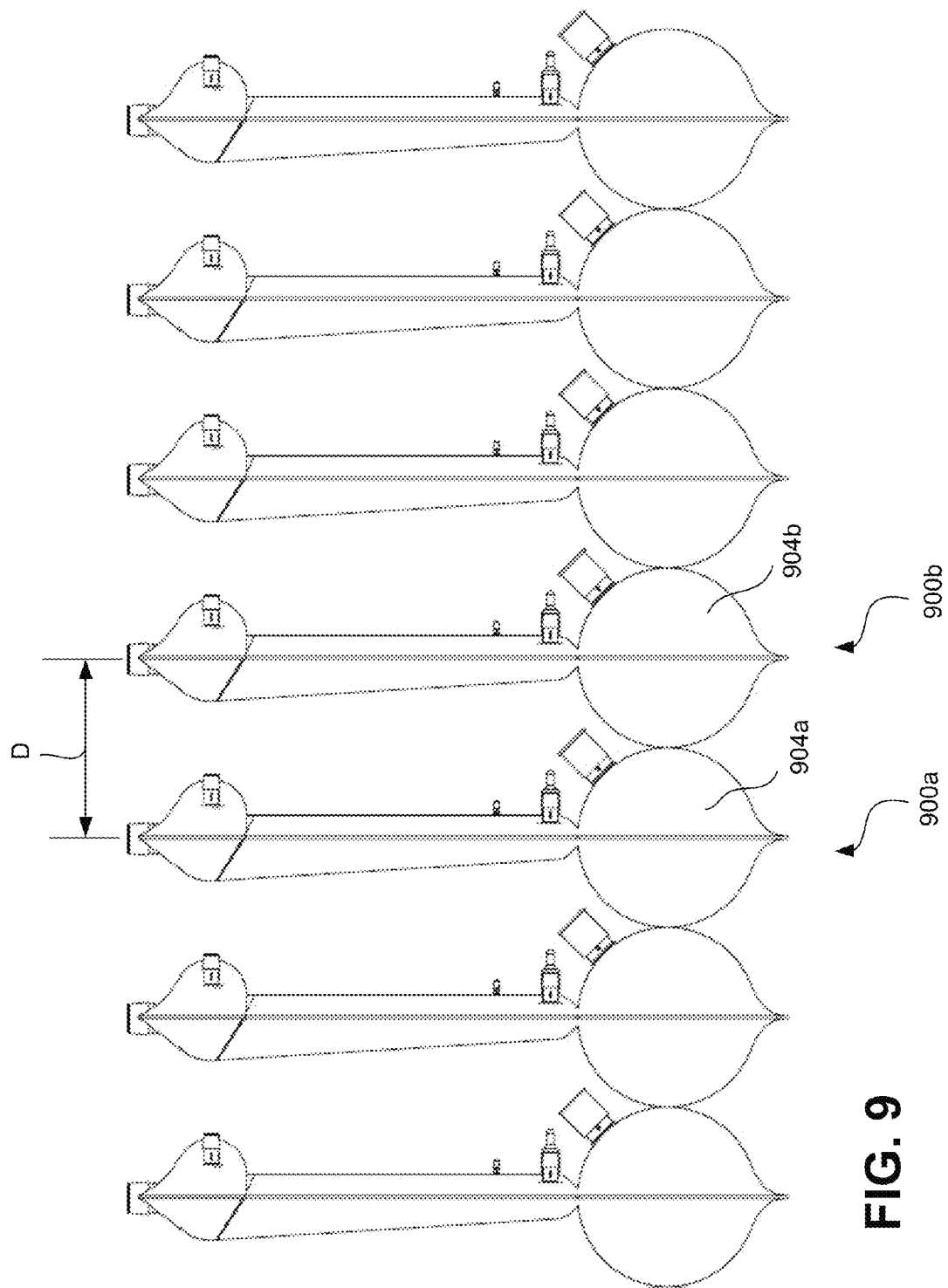
FIG. 9 illustrates an end view of a plurality of photobioreactors placed side-by-side, according to embodiments of the present invention.

The ballast containment 104 size and/or diameter can be made to provide a mechanism for controlling the separation distance D between adjacent vessels 900a, 900b, as illustrated in FIG. 9. In this way, the ballast tube 104 can serve two functions, thereby reducing cost: to control light exposure and to govern separation distance between panels, according to embodiments of the present invention.

The nature of the floating vessel enables a configuration that responds to wave action in a basin and lagoon in the form of mixing of the algal broth, according to embodiments of the present invention. This is a very low cost form a energy available to mix the algal broth to increase or sustain high growth rates and reduce or eliminate sparging energy consumption, according to embodiments of the present invention.

Various vessels 101, 102, 104 of the photobioreactor 100 can have strategically placed reinforcing materials applied to each containment area and/or use thicker materials to provide the robustness to survive inclement weather and wave action in a large body of water, lake or ocean, according to embodiments of the present invention. For example, the bottom surface 802 of the ballast chamber 104 may be reinforced, as discussed above.

As shown in FIGS. 10 and 11, the top of the photobioreactor 100 may include one or more flaps 1002, 1004, or extensions of the buoyancy containment vessel 102, which may be constructed from either the containment material or some other floating plastic material that is attachable to the parent material in order to serve as a segmented cover that overlaps the adjacent photobioreactor 100, according to embodiments of the present invention. Alternatively, instead of overlapping an adjacent photobioreactor, such top flaps 1002, 1004 may simply cover the top surface of the water between adjacent photobioreactors 100, according to embodiments of the present invention. Such flaps or extensions may minimize evaporation, thereby conserving water use, according to embodiments of the present invention. Such a configuration presents a very inexpensive method for minimizing evaporation, because the material cost can be very low and minimal labor would be needed compared to installation of separate covers to retain heat or minimize evaporation. Such flaps 1002, 1004 may also be used as an alternative way to maintain proper panel spacing, according to embodiments of the present invention. FIG. 11 illustrates a plurality of adjacently-positioned photobioreactors 100 with top flaps 1002, 1004 extending toward adjacent photobioreactors 100, according to embodiments of the present invention.

FIG. 12 illustrates an alternative photobioreactor 1200, according to embodiments of the present invention. Photobioreactor 1200 includes fixed air pockets 1202 which may be welded into the side of the basic panel material. According to some embodiments of the present invention, air cannot be inserted into or removed from the fixed air pockets 1202, so they may be formed with a small enough volume to permit the control of the depth of the photobioreactor 1200 to be controlled based on the ballast 104 volume and/or the sparge rate. Between the fixed air pockets 1202 are sparge gas pockets 1204, which are areas that contain the sparge gas 1208 after it has been bubbled through the growth chamber and before it is exhausted, according to embodiments of the present invention. An exhaust opening 1206 may be formed at the top of one or more sparge gas pockets 1204, to permit the sparge gas 1208 to exit the photobioreactor 1200, according to embodiments of the present invention. These exhaust openings 1206 may be formed by leaving a top edge of the photobioreactor material layers unwelded, for example. According to one embodiment of the present invention, two or more of fixed air pockets 1202 may be in fluid communication with one another.

Figure 14:
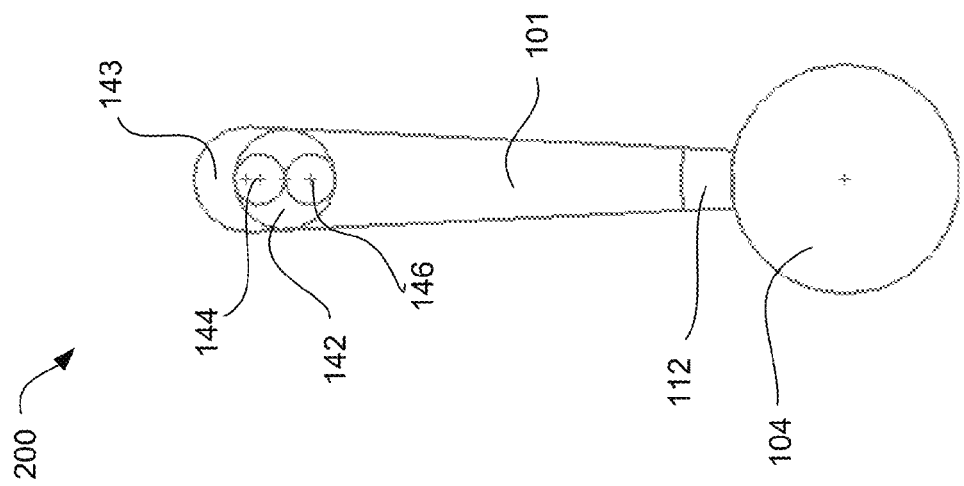
FIG. 14 illustrates a sectional end view of the photobioreactor of FIG. 13, according to embodiments of the present invention.
Figure 13:
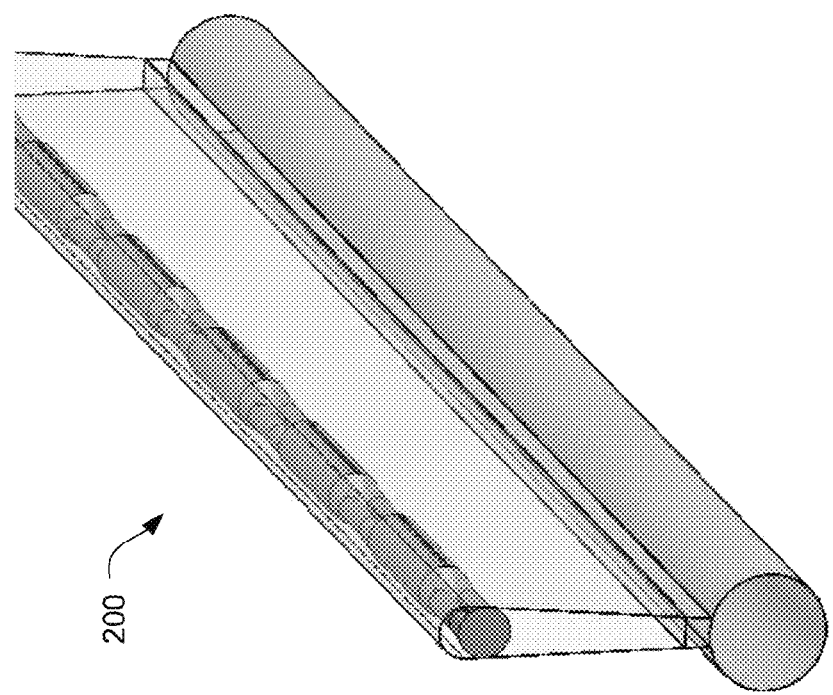
FIG. 13 illustrates a partial cross-sectional perspective view of another alternative photobioreactor, according to embodiments of the present invention.
Figure 15:
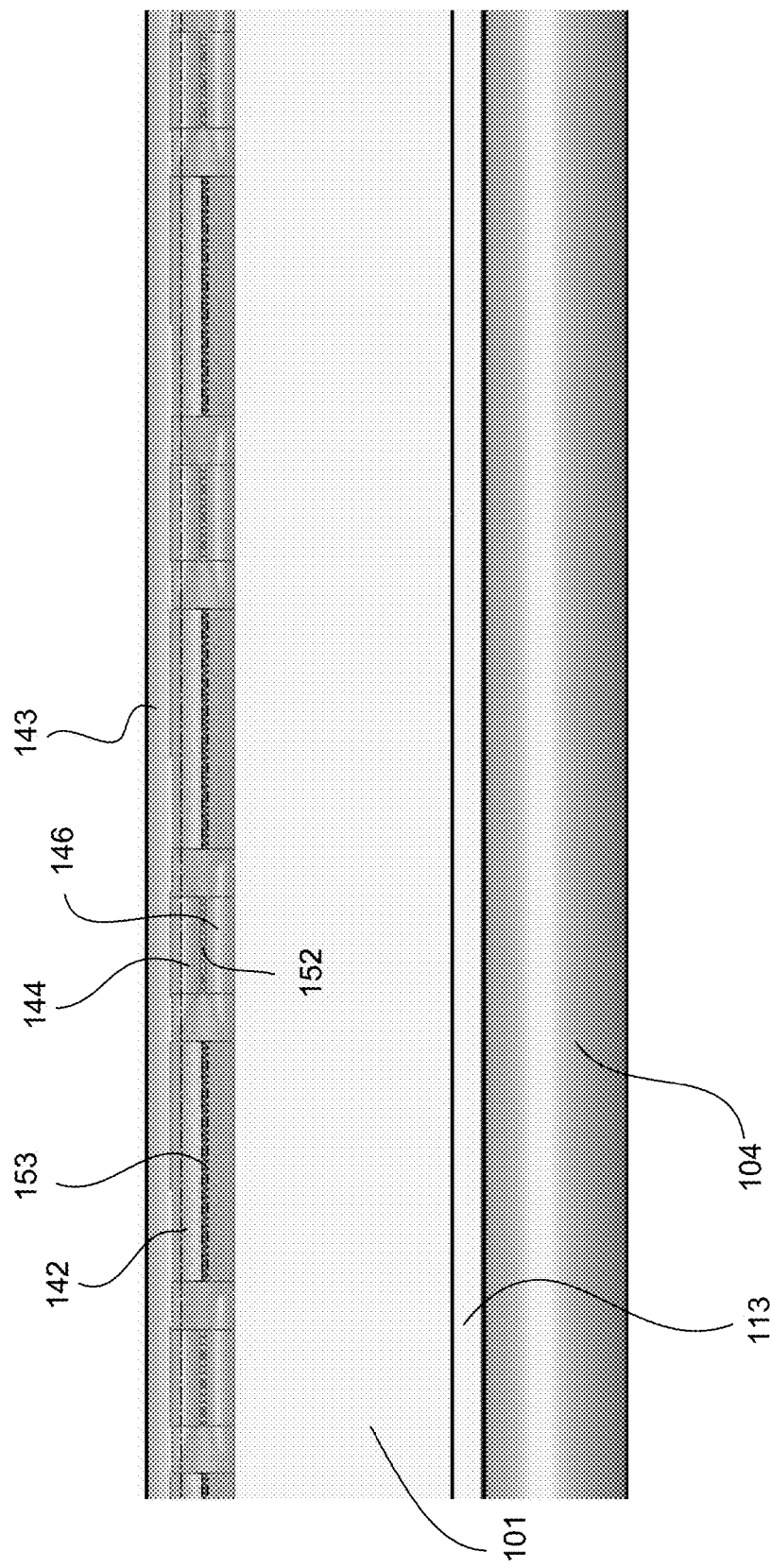
FIG. 15 illustrates a side elevation view of the photobioreactor of FIGS. 13 and 14, according to embodiments of the present invention.
Figure 16:
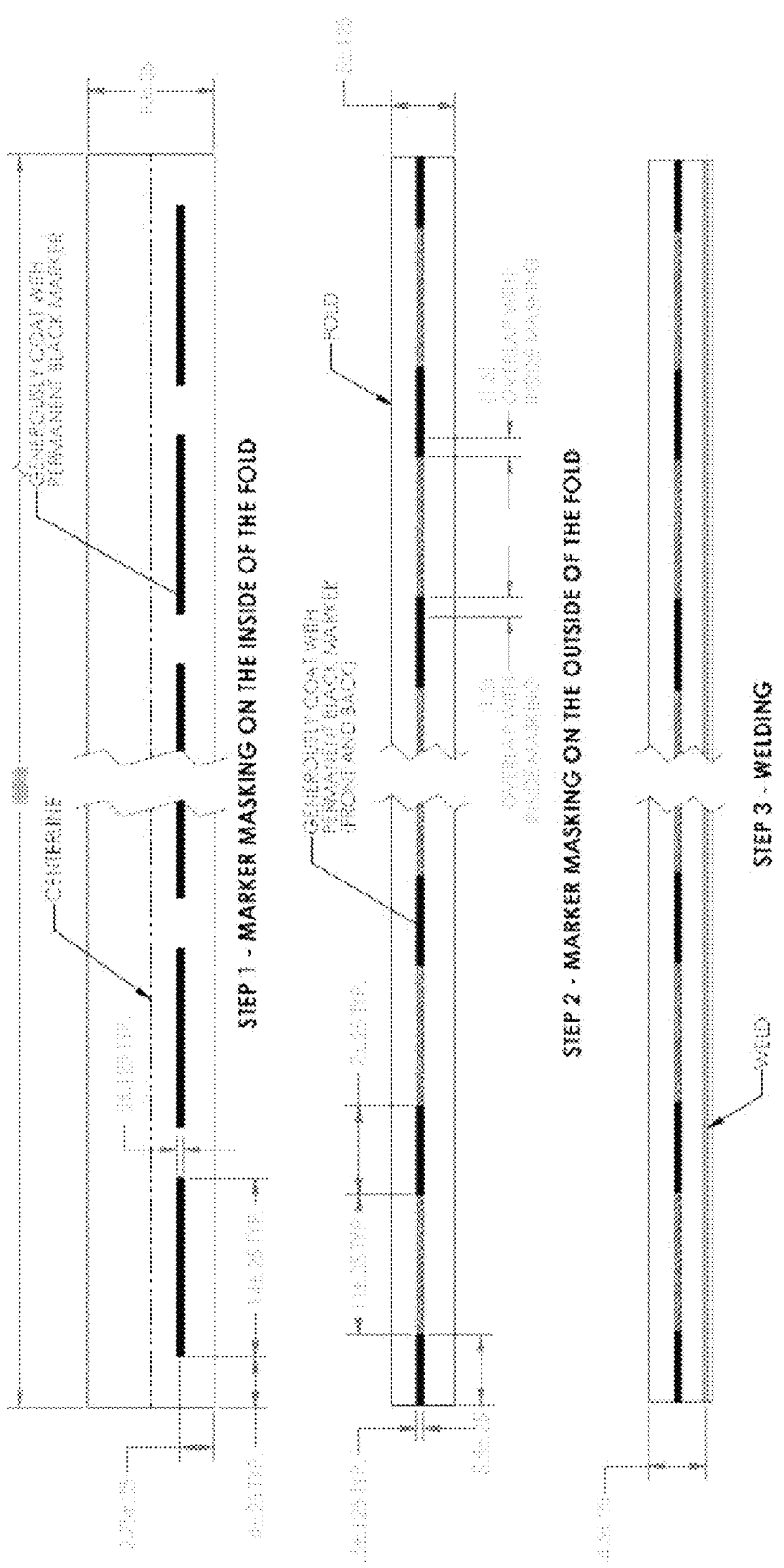
FIG. 16 illustrates three steps for forming the photobioreactor of FIGS. 13 through 15, according to embodiments of the present invention.
Figure 17:
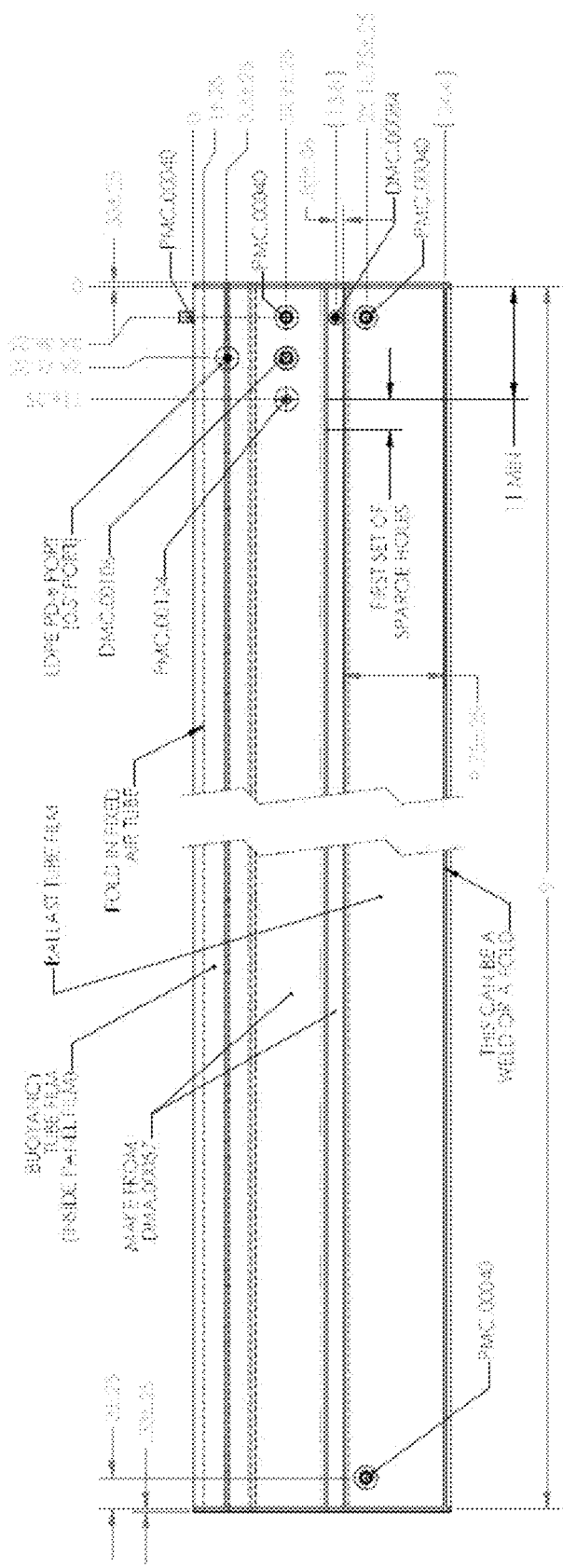
FIG. 17 illustrates port placement during construction of the photobioreactor of FIGS. 13 through 15, according to embodiments of the present invention.

FIG. 13 illustrates a partial cross-sectional perspective view of another alternative photobioreactor 200, according to embodiments of the present invention. Photobioreactor 200 is similar to photobioreactor 100; however, photobioreactor 200 is more symmetrical, which is made possible by a buoyancy tube which alternates along the length of the photobioreactor 200 between a full diameter tube 142 and a set of two smaller tubes 144, 146, one on top of the other, according to embodiments of the present invention. The head space 143 is located above the buoyancy tubes 142, 144, 146, and the sparge gas from the sparge chamber 112 is permitted to pass through the buoyancy tube into the head space 143 at the locations of the smaller-diameter buoyancy tubes 144, 146, according to embodiments of the present invention. This buoyancy tube with an alternating pattern may be formed by using multiple (e.g. four) layers of plastic liner, and placing selective weld lines across the length, both before and after folding and/or overlapping the layers. Ink (e.g. marker ink) placed on the film prevents welding of the layers at selected locations in order to form the various chambers and structures, as illustrated in FIG. 16. For example, the welds 152 on the inside layers essentially create the dividing line between buoyancy tube 144 and buoyancy tube 146, while welds 153 on the outside layer essentially create the larger diameter buoyancy tubes 142, according to embodiments of the present invention. FIG. 16 further illustrates three steps for forming the photobioreactor of FIGS. 13-15, according to embodiments of the present invention, and FIG. 17 illustrates port placement during construction of the photobioreactor of FIGS. 13-15, according to embodiments of the present invention.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A photobioreactor system comprising:
a reservoir containing liquid, the liquid having a top surface level;
a photobioreactor, wherein the photobioreactor is flexible and is floating in the liquid, the photobioreactor comprising:
a growth chamber containing media in which organisms may be grown; and
a ballast chamber containing a fluid, the fluid having an effective density greater than that of the liquid, such that the ballast chamber exerts a force on the photobioreactor in a downward direction;
wherein the photobioreactor is one of a plurality of photobioreactors each substantially the same as the photobioreactor, wherein the plurality of photobioreactors is floating in the liquid, and wherein the plurality of photobioreactors are positioned one next to the other such that a spacing between two adjacent photobioreactors of the plurality of photobioreactors is determined by widths of adjacent abutting ballast chambers.

2. The photobioreactor system of claim 1, wherein the fluid is a first fluid, wherein the effective density is a first effective density, wherein the force is a first force, and wherein the photobioreactor further comprises:
a buoyancy chamber containing a second fluid, the second fluid having a second effective density less than that of the liquid, such that the buoyancy chamber exerts a second force on the photobioreactor in an upward direction.

3. The photobiorector system of claim 2, wherein the photobioreactor further comprises:
a sparging chamber having a plurality of holes opening into the growth chamber, the sparging chamber containing a sparging gas or gas mixture that is configured to pass through the plurality of holes and rise through the media.

4. The photobiorector system of claim 3, wherein the top surface level is a reservoir top surface level, wherein the growth chamber comprises a head space above a media top surface level, and wherein the head space accommodates accumulation of the sparging gas or gas mixture.

5. The photobioreactor system of claim 4, wherein the buoyancy chamber is isolated from, and directly adjacent to, the head space.

6. The photobioreactor system of claim 5, wherein the ballast chamber is isolated from, and directly adjacent to, a bottom of the growth chamber.

7. The photobioreactor system of claim 5, wherein the sparging chamber is located at a bottom of the growth chamber, and wherein the ballast chamber is isolated from, and directly adjacent to, the sparging chamber.

8. The photobioreactor system of claim 2, wherein the ballast chamber and the buoyancy chamber maintain the photobioreactor in a substantially upright position as the photobioreactor is floating in the liquid.

9. The photobioreactor system of claim 2, wherein the first fluid is salt water, and the second fluid is air.

10. The photobioreactor system of claim 2, wherein the buoyancy chamber comprises at least one port through which the second fluid may be added to or removed from the buoyancy chamber.

11. The photobioreactor system of claim 1, wherein the reservoir is a body of water selected from the group consisting of: an ocean, a lake, a sea, a pond, a river, a basin, a tub, a pool, and a tank.

12. The photobioreactor system of claim 1, wherein the reservoir is a naturally occurring body of water.

13. The photobioreactor system of claim 12, wherein the fluid is salt water.

14. The photobioreactor system of claim 1, wherein the ballast chamber comprises at least one port through which the fluid may be added to or removed from the ballast chamber.

15. The photobioreactor system of claim 1, wherein each of the plurality of photobioreactors comprises a top flap, wherein the top flap is configured to be placed over a top of an adjacent photobioreactor or over the top surface level of the liquid between adjacent photobioreactors.

16. The photobioreactor system of claim 15, wherein the photobioreactor is at least partially formed of a substantially transparent plastic film.

17. The photobioreactor system of claim 15, wherein the photobioreactor is at least partially formed of or coated by an anti-biofouling additive selected from the group consisting of: polyethylene glycol (PEG), hyperbranched fluoropolymer (HBFP), polyethylene (PE), polyvinyl chloride (PVC), polymethylmethacrylatc (PMMA), natural rubber (NR), polydimethylsiloxane (PDMS), polystyrene (PS), perfluoropolyether (PFPE), polytetrafluoroethylene (PTFE), and silicons and derivatives.

18. The photobioreactor system of claim 15, wherein the media comprises an anti-biofouling additive selected from the group consisting of: polyethylene glycol (PEG), silicons and derivatives, biocides, fluorocarbons, and quatinary amines.

19. The photobioreactor system of claim 1, wherein the photobioreactor is at least partially formed of a substantially transparent plastic film.

20. The photobioreactor system of claim 19, wherein at least a bottom surface of the ballast chamber is reinforced to minimize possible puncture.

21. The photobioreactor system of claim 1, wherein the photobioreactor is at least partially formed of or coated by an anti-biofouling additive selected from the group consisting of: polyethylene glycol (PEG), hyperbranched fluoropolymer (HBFP), polyethylene (PE), polyvinyl chloride (PVC), polymethylmethacrylatc (PMMA), natural rubber (NR), polydimethylsiloxane (PDMS), polystyrene (PS), perfluoropolyether (PFPE), polytetrafluoroethylene (PTFE), and silicons and derivatives.

22. The photobioreactor system of claim 21, wherein at least a bottom surface of the ballast chamber is reinforced to minimize possible puncture.

23. The photobioreactor system of claim 1, wherein the media comprises an anti-biofouling additive selected from the group consisting of: polyethylene glycol (PEG), silicons and derivatives, biocides, fluorocarbons, and quatinary amines.

24. The photobioreactor system of claim 1, wherein at least a bottom surface of the ballast chamber is reinforced to minimize possible puncture.

25. The photobioreactor system of claim 1, wherein the fluid is salt water.

26. The photobioreactor system of claim 1, wherein the ballast chamber is isolated from, and directly adjacent to, a bottom of the growth chamber.

\* \* \* \* \*